United States Patent
Grill et al.

(10) Patent No.: US 11,890,477 B2
(45) Date of Patent: Feb. 6, 2024

(54) SYSTEMS AND METHODS FOR SPINAL CORD STIMULATION

(71) Applicant: Duke University, Durham, NC (US)

(72) Inventors: Warren M. Grill, Durham, NC (US); Tianhe Zhang, Durham, NC (US)

(73) Assignee: Duke University, Durham, NC (US)

( * ) Notice: Subject to any disclaimer, the term of this patent is extended or adjusted under 35 U.S.C. 154(b) by 337 days.

(21) Appl. No.: 17/313,113

(22) Filed: May 6, 2021

(65) Prior Publication Data

US 2021/0252290 A1   Aug. 19, 2021

Related U.S. Application Data

(63) Continuation of application No. 16/276,680, filed on Feb. 15, 2019, now Pat. No. 11,013,922, which is a continuation of application No. 15/454,484, filed on Mar. 9, 2017, now Pat. No. 10,213,605, which is a continuation of application No. PCT/US2015/052487, filed on Sep. 25, 2015.

(60) Provisional application No. 62/055,798, filed on Sep. 26, 2014.

(51) Int. Cl.
*A61N 1/36* (2006.01)
*G16H 50/50* (2018.01)
*G16Z 99/00* (2019.01)
*A61N 1/372* (2006.01)

(52) U.S. Cl.
CPC ..... *A61N 1/36139* (2013.01); *A61N 1/36071* (2013.01); *A61N 1/36132* (2013.01); *A61N 1/37217* (2013.01); *A61N 1/37247* (2013.01); *G16H 50/50* (2018.01); *G16Z 99/00* (2019.02)

(58) Field of Classification Search
CPC ............ A61N 1/36071; A61N 1/36132; A61N 1/36139; A61N 1/37217; A61N 1/37247; G16H 50/50; G16Z 99/00
See application file for complete search history.

(56) References Cited

U.S. PATENT DOCUMENTS

| | | |
|---|---|---|
| 10,213,605 B2 | 2/2019 | Grill et al. |
| 2002/0038294 A1 | 3/2002 | Matsugu |
| 2006/0015153 A1 | 1/2006 | Gliner et al. |
| 2006/0095081 A1 | 5/2006 | Zhou et al. |
| 2010/0152807 A1 | 6/2010 | Grill et al. |
| 2010/0191307 A1 | 7/2010 | Fang et al. |
| 2011/0184488 A1 | 7/2011 | De Ridder |
| 2013/0231715 A1 | 9/2013 | Grill, Jr. et al. |
| 2014/0081346 A1* | 3/2014 | Eguibar ............... A61N 1/0526 607/45 |

* cited by examiner

*Primary Examiner* — George Manuel
(74) *Attorney, Agent, or Firm* — NK Patent Law

(57) ABSTRACT

A system for delivering electrical pulse stimulation to a subject includes a remote control device configured to at least intermittently transmit temporal pulse pattern programming and a stimulation device comprising a control interface, at least one electrode in electrical communication with the control interface, and an input device in at least intermittent communication with the remote control device to receive the temporal pulse pattern programming. The stimulation device is configured to deliver electrical pulse stimulation to a subject via the at least one electrode according to the temporal pulse pattern programming.

24 Claims, 12 Drawing Sheets

SYSTEMS AND METHODS FOR SPINAL CORD STIMULATION

CROSS-REFERENCE TO RELATED APPLICATION

This application is a continuation of U.S. patent application Ser. No. 16/276,680, filed on Feb. 15, 2019, which is a continuation application of U.S. patent application Ser. No. 15/454,484, filed on Mar. 9, 2017, issued as U.S. Pat. No. 10,213,605 on Feb. 26, 2019, which is a continuation of PCT patent application no. PCT/US2015/052487 titled "SYSTEMS AND METHODS FOR SPINAL CORD STIMULATION", filed on Sep. 25, 2015, which claims the benefit of priority of U.S. provisional patent application No. 62/055,798 titled "Systems and Methods for Optimized Spinal Cord stimulation", filed on Sep. 26, 2014, all of which are incorporated herein in their entirety by this reference.

TECHNICAL FIELD

The presently disclosed subject matter relates to spinal cord stimulation, and more specifically, to administering spinal cord stimulation (SCS) based on temporal patterns of electrical stimulation with considerations toward efficacy, efficiency and side effects.

BACKGROUND

Spinal cord stimulation (SCS) has emerged as a potential viable means of managing chronic pain whereas other treatment means such as kinetic (physical rehabilitation), pharmaceutical, and surgical therapies have not been effective. Studies of the clinical success of SCS, however, have been highly variable and recent years have shown very little improvement in its success. Conventional clinical SCS is typically accompanied by side-effects including paresthesias, or tingling sensations associated with neural activation of the dorsal columns, over the region of pain. These paresthesias may adversely affect patient satisfaction with therapy and compliance. Efforts to improve clinical efficacy of SCS and to reduce paresthesias associated with SCS have not focused on the effect of SCS on the activity of neurons in the dorsal horn pain processing circuit. Recently, novel methods of SCS, including pulsed SCS and high frequency SCS have been claimed to provide pain relief comparable to clinical SCS with significantly reduced paresthesias. These approaches, however, may be suboptimal, as they neither search for nor implement parameters that have been algorithmically determined to be optimal for efficacy (reduction of neural activity associated with pain relief), efficiency (power consumption), and paresthesia reduction.

SCS therapy involves the epidural implantation of an electrode that is connected to a controller capable of delivering electrical stimulation to neural elements in the spinal cord responsible for the modulation and transmission of pain to the brain. However, SCS programmers are currently only capable of configuring SCS devices to deliver constant inter-pulse interval (IPI) stimulation. Recent developments in SCS feature technologies that have been claimed to be able to provide pain relief with reduced side effects, but these methods do not use or provide a means to set stimulation parameters that are optimized for efficacy, efficiency, and side effect reduction. No prior technology includes a device that has the capability of remotely programming an SCS delivery device with optimized non-regular temporal patterns or multiple frequency combinations through one or multiple electrode contacts.

SUMMARY

This summary is provided to introduce, in a simplified form, concepts that are further described in the following detailed descriptions. This Summary is not intended to identify key features or essential features of the claimed subject matter, nor is it to be construed as limiting the scope of the claimed subject matter.

In at least one embodiment, a method of optimizing temporal pulse patterns for stimulation delivery to a subject includes: generating a first generation temporal pulse pattern; delivering stimulation according to the first generation temporal pulse pattern to a subject; measuring efficacy, efficiency and side-effect parameters affected by the delivered stimulation; determining a fitness of the first generation temporal pulse pattern using the measured efficacy, efficiency and side-effect parameters; generating a second generation temporal pulse pattern using the first generation temporal pulse pattern according to the determined fitness of the first generation temporal pulse pattern; and delivering stimulation according to the second generation temporal pulse pattern to the subject.

In at least one example, the method includes iteratively: delivering stimulation to the subject according to any particular generation temporal pulse pattern; measuring efficacy, efficiency and side-effect parameters affected by delivery of the stimulation to the subject according to the particular generation temporal pulse pattern; determining a fitness of the particular generation temporal pulse pattern using the measured efficacy, efficiency and side-effect parameters thereof; and generating a next generation temporal pulse pattern using the particular generation temporal pulse pattern according to the determined fitness of the particular generation temporal pulse pattern.

In at least one example, generating the next generation temporal pulse pattern includes crossing the particular generation temporal pulse pattern with at least one other temporal pulse pattern.

In at least one example, a probability of any pulse in the next generation temporal pulse pattern originating from either the particular generation temporal pulse pattern or the at least one other temporal pulse pattern is independent of that of any other pulse.

In at least one example, crossing the particular generation temporal pulse pattern with at least one other temporal pulse pattern generates an offspring temporal pulse pattern, and generating the next generation temporal pulse pattern includes adding at least one point mutation to the offspring temporal pulse pattern.

In at least one example, generating a next generation temporal pulse pattern further includes using random patterns.

In at least one example, the subject includes a physical subject; and delivering stimulation to the subject includes delivering electrical pulses to the physical subject.

In at least one example, the subject includes a computational model; and delivering stimulation to the subject includes simulating delivery of pulses to the computational model.

In at least one example, the method further includes, for each simulated delivery of pulses to the computational model, measuring efficacy, efficiency and side-effect parameters.

In at least one example, the subject includes a computational model; and delivering stimulation to the subject includes simulating delivery of pulses to the computational model.

In at least one example, the computational model includes a network of simulated biophysical neurons connected in a manner consistent with a physical dorsal horn pain processing neuron network.

In at least one example, the computational model incorporates delays based on the conduction velocities of neuron fibers to simulate signal propagation from a peripheral or dorsal column nerve fiber.

In at least one example, the computational model includes representations of neurons in the dorsal column nuclei (DCN).

In at least one example, the first generation temporal pulse pattern is generated by simulating delivery of pulses to a computational model; and delivering stimulation according to the first generation temporal pulse pattern to a subject includes delivering electrical pulses to a physical subject.

In at least one example, measuring efficacy, efficiency and side-effect parameters affected by the delivered stimulation includes measuring efficacy by determining reduction of neural activity associated with pain relief.

In at least one example, measuring efficacy, efficiency and side-effect parameters affected by the delivered stimulation includes measuring an efficacy parameter by determining the difference between an average firing rate of a neuron while delivering stimulation according to the first generation temporal pulse pattern and the firing rate of the neuron during constant frequency stimulation with which the first generation temporal pulse pattern has the same average frequency.

In at least one example, measuring efficacy, efficiency and side-effect parameters affected by the delivered stimulation includes measuring an efficiency parameter by determining the average frequency of the first generation temporal pulse pattern.

In at least one example, measuring efficacy, efficiency and side-effect parameters affected by the delivered stimulation includes measuring a side effect parameter by determining an average side effect firing rate of neurons.

In at least one example, determining a fitness of the first generation temporal pulse pattern using the measured efficacy, efficiency and side-effect parameters includes minimizing a cost function (J) defined as $J=A \times F + B \times S + C \times P$; wherein: A, B, and C are numerical coefficients; F is the efficacy parameter; S is the efficiency parameter; and P is the side effect parameter.

In at least one example, the subject is a human patient and the side effect parameter is determined at least in part using feedback from the human patient.

In at least one example, generating a first generation temporal pulse pattern includes iteratively generating multiple prior generations of temporal pulse patterns using a computational model.

In at least one example, each prior generation temporal pulse pattern is used to deliver simulated stimulation to the computational model and efficacy, efficiency and side-effect parameters are measured by calculation to determine fitness for use of the prior generation temporal pulse pattern in generating subsequent generation temporal pulse patterns.

In at least one example, each temporal pulse pattern includes pulses each having an adjustable duration and amplitude.

In at least one example, the amplitude corresponds to voltage or current.

In at least one embodiment, a method of optimizing temporal pulse patterns for stimulation delivery to a patient includes: generating temporal pulse pattern sets using a computational model by simulating delivery of pulse patterns to the computational model and iteratively constructing successive generations of the pulse patterns by determining fitness of each particular pulse pattern and crossing those pulse patterns determined as fit; saving the generated temporal pulse pattern sets for selection by a user; and delivering electrical pulse stimulation to a patient according to a selection made the user of one or more of the saved temporal pulse pattern sets.

In at least one example, the method further includes iteratively constructing successive generations of temporal pulse pattern sets by: delivering electrical pulse stimulation to the patient according to any particular generation temporal pulse pattern set; measuring efficacy, efficiency and side-effect parameters affected by the delivery of electrical pulse stimulation to the patient according to the particular generation temporal pulse pattern set; determining a fitness of the particular generation temporal pulse pattern set using the measured efficacy, efficiency and side-effect parameters thereof; and generating a next generation temporal pulse pattern set using the particular generation temporal pulse pattern set according to the determined fitness of the particular generation temporal pulse pattern set.

In at least one example, the method further includes iteratively constructing successive generations of temporal pulse pattern sets by: delivering electrical pulse stimulation to the patient according to any particular generation temporal pulse pattern set; measuring efficacy, efficiency and side-effect parameters affected by the delivery of electrical pulse stimulation to the patient according to the particular generation temporal pulse pattern set; determining a fitness of the particular generation temporal pulse pattern set using the measured efficacy, efficiency and side-effect parameters thereof; and generating a next generation temporal pulse pattern set using the particular generation temporal pulse pattern set according to the determined fitness of the particular generation temporal pulse pattern set.

In at least one example, each temporal pulse pattern set includes pulses each having an adjustable duration and amplitude.

In at least one example, the amplitude corresponds to voltage or current.

In at least one embodiment, a system for delivering electrical pulse stimulation to a subject includes: a remote control device configured to at least intermittently transmit temporal pulse pattern programming; and a stimulation device including a control module, at least one electrode in electrical communication with the control module, and an input device in at least intermittent communication with the remote control device to receive the temporal pulse pattern programming, the stimulation device configured to deliver electrical pulse stimulation to a subject via the at least one electrode according to the temporal pulse pattern programming.

In at least one example, the at least one electrode includes multiple electrodes each for placement in proximity to a respective portion of the subject.

In at least one example, the temporal pulse pattern programming includes respective instructions for delivery of electrical pulse stimulation by each of the multiple electrodes.

In at least one example, the remote control device is configured to at least intermittently wirelessly transmit temporal pulse pattern programming, and the input device of the stimulation device at least intermittent communicates wirelessly with the remote control device to receive the temporal pulse pattern programming.

In at least one example, the remote control device and the stimulation device communicate through at least one of: radiofrequency (RF) transmission; Bluetooth transmission; and a wireless local area network (WLAN).

In at least one example, the system includes a processor configured to generate the temporal pulse pattern programming by optimizing temporal pulse patterns by: generating temporal pulse patterns using a computational model by simulating delivery of pulse patterns to the computational model and iteratively constructing successive generations of the pulse patterns by determining fitness of each particular pulse pattern and crossing the pulse patterns that are determined to be fit.

In at least one example, the processor is configured to optimize the temporal pulse patterns by further iteratively constructing successive generations of temporal pulse pattern sets by: causing delivery of electrical pulse stimulation to the subject according to any particular generation of temporal pulse patterns; measuring efficacy, efficiency and side-effect parameters affected by the delivery of electrical pulse stimulation to the subject according to the particular generation temporal pulse patterns; determining a fitness of the particular generation temporal pulse patterns using the measured efficacy, efficiency and side-effect parameters thereof; and generating a next generation temporal pulse patterns using the particular generation temporal pulse patterns according to the determined fitness of the particular generation temporal pulse patterns.

In at least one example, each of the temporal pulse patterns includes instructions to deliver pulses each having an adjustable duration and amplitude.

In at least one example, the amplitude corresponds to voltage or current.

In at least one example, the processor is an onboard component of the remote control device.

In at least one example, the processor is an onboard component of the stimulation device.

In at least one example, the processor downloads the temporal pulse pattern programming to the remote control device.

In at least one example, the remote control device is configured to generate the temporal pulse pattern programming.

In at least one example, the remote control device is configured to receive and store the temporal pulse pattern programming.

In at least one example, the temporal pulse pattern programming includes multiple temporal pulse pattern sets, and wherein the remote control device includes a user input device by which a user selects particular ones of the multiple temporal pulse pattern sets to be transmitted to the stimulation device.

In at least one embodiment, a remote control device is provided for a system for delivering electrical pulse stimulation to a subject, the system including a stimulation device including a control module, at least one electrode in electrical communication with the control module, and an input device by which to receive temporal pulse pattern programming, the stimulation device configured to deliver electrical pulse stimulation to a subject via the at least one electrode according to the temporal pulse pattern programming. The remote control device is configured to at least intermittently transmit the temporal pulse pattern programming.

In at least one example, the temporal pulse pattern programming includes respective instructions for delivery of electrical pulse stimulation by each of multiple electrodes.

In at least one example, the remote control device is configured to wirelessly transmit the temporal pulse pattern programming.

In at least one example, the remote control device and the stimulation device communicate through at least one of: radiofrequency (RF) transmission; Bluetooth transmission; and a wireless local area network (WLAN).

In at least one example, the system further includes a processor configured to generate the temporal pulse pattern programming by optimizing temporal pulse patterns by: generating temporal pulse patterns using a computational model by simulating delivery of pulse patterns to the computational model and iteratively constructing successive generations of the pulse patterns by determining fitness of each particular pulse pattern and crossing the pulse patterns that are determined to be fit.

In at least one example, the processor is configured to optimize the temporal pulse patterns by further iteratively constructing successive generations of temporal pulse pattern sets by: causing delivery of electrical pulse stimulation to the subject according to any particular generation of temporal pulse patterns; measuring efficacy, efficiency and side-effect parameters affected by the delivery of electrical pulse stimulation to the subject according to the particular generation temporal pulse patterns; determining a fitness of the particular generation temporal pulse patterns using the measured efficacy, efficiency and side-effect parameters thereof; and generating a next generation temporal pulse patterns using the particular generation temporal pulse patterns according to the determined fitness of the particular generation temporal pulse patterns.

In at least one example, each of the temporal pulse patterns includes instructions to deliver pulses each having an adjustable duration and amplitude.

In at least one example, the amplitude corresponds to voltage or current.

In at least one example, the processor is an onboard component of the remote control device.

In at least one example, the processor is an onboard component of the stimulation device.

In at least one example, the processor downloads the temporal pulse pattern programming to the remote control device.

In at least one example, the remote control device is configured to generate the temporal pulse pattern programming.

In at least one example, the remote control device is configured to receive and store the temporal pulse pattern programming.

In at least one example, the temporal pulse pattern programming includes multiple temporal pulse pattern sets, and wherein the remote control device includes a user input device by which a user selects particular ones of the multiple temporal pulse pattern sets to be transmitted to the stimulation device.

BRIEF DESCRIPTION OF THE DRAWINGS

The previous summary and the following detailed descriptions are to be read in view of the drawings, which illustrate particular exemplary embodiments and features as briefly described below. The summary and detailed descriptions, however, are not limited to only those embodiments and features explicitly illustrated.

DETAILED DESCRIPTIONS

Figure 1:
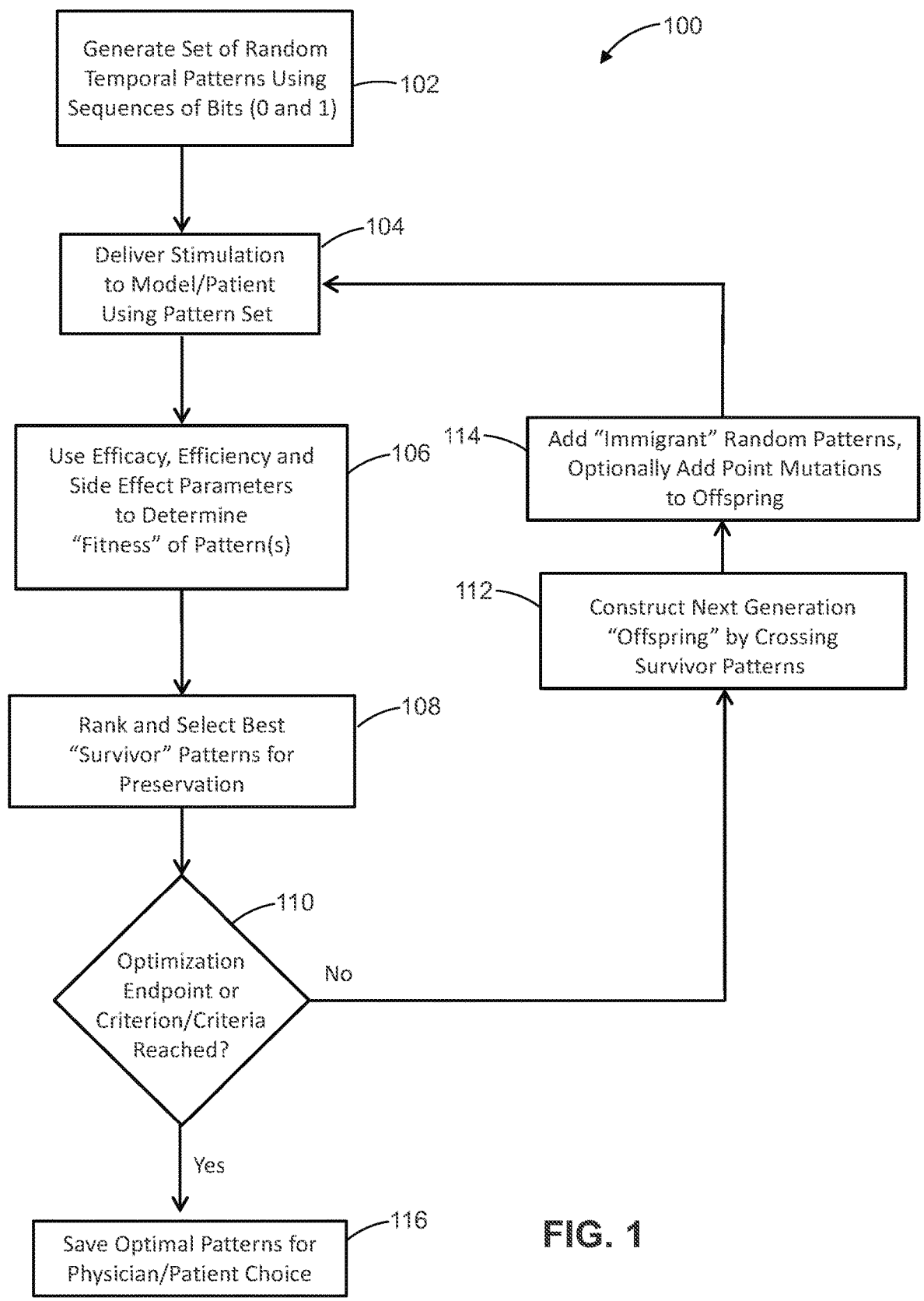
FIG. 1 is a flow chart of a method of model-based design of optimal temporal patterns of pulse stimulation.

These descriptions are presented with sufficient details to provide an understanding of one or more particular embodiments of broader inventive subject matters. These descriptions expound upon and exemplify particular features of those particular embodiments without limiting the inventive subject matters to the explicitly described embodiments and features. Considerations in view of these descriptions will likely give rise to additional and similar embodiments and features without departing from the scope of the inventive subject matters. Although the term "step" may be expressly used or implied relating to features of processes or methods, no implication is made of any particular order or sequence among such expressed or implied steps unless an order or sequence is explicitly stated.

Any dimensions expressed or implied in the drawings and these descriptions are provided for exemplary purposes. Thus, not all embodiments within the scope of the drawings and these descriptions are made according to such exemplary dimensions. The drawings are not made necessarily to scale.

These descriptions relate to the use of a search heuristic (genetic algorithm) coupled with a biophysical model of the pain circuit in the spinal cord to optimize the temporal patterning of SCS in such a way as to suppress the transmission of nociceptive information from the spinal cord (efficacy), reduce power consumption (efficiency), and reduce neural signals associated with side-effect paresthe- sias. Computational modeling work indicates that the activity of wide-dynamic range (WDR) neurons in the spinal cord that transmit nociceptive information (pain signals) to the brain is dependent on the frequency of applied SCS, suggesting that novel temporal patterns of SCS could be used to minimize both WDR neuron activity (mitigation of pain) and the frequency of applied stimulation (reduction in power consumption and possible side effects). Optimization of pain suppression using temporal patterning with the optimization and use of temporal patterning to suppress paresthesias in addition to pain relief is described.

The genetic algorithm uses the output of a computational model consisting of dorsal horn wide-dynamic range (WDR) projection neurons responsible for transmitting nociceptive information to the brain and dorsal column nuclei (DCN) neurons associated with side-effect paresthesias to optimize the temporal pattern of stimulation delivered during SCS. Such optimized stimulation will suppress the activity of both WDR and DCN neurons as much as possible and at the lowest possible frequency. Furthermore, the relative importance of reducing WDR activity (efficacy), reducing stimulation frequency (efficiency), and reducing DCN neuron activity (paresthesias) can be controlled by modifying the weights on F, S, and P in Equation (1) as described below to generate a family of optimized stimulation patterns tailored to user or patient-specific application. The algorithm may be carried out continuously and as part of the software of an SCS pulse generator. Patient ratings of pain and paresthesia can be used as proxies for WDR and DCN activity, respectively.

Optimization occurs using a search heuristic genetic algorithm (GA) in which optimal stimulation patterns are developed and evaluated over several iterations, or "generations." In the algorithm, each stimulation pattern under testing is represented as a "gene" including a series of bits representing whether stimulation is on or off over the time interval represented by each pulse. Stimulation occurs according to the stream of pulses represented by each pattern within the set of possible patterns for a previously established period of time, after which the "fitness" of the pattern is evaluated. The best patterns as determined by a cost function that favors a combination of low WDR/DCN neuronal output and low stimulation frequency are kept, and genes of different surviving patterns are crossed to generate "offspring" patterns for further trials. Furthermore, to introduce variability into the stimulation patterns for the purpose of facilitating convergence to an optimal solution, point mutations can be intermittently applied to the elements in the "offspring" that define the pulse train, and "immigrants" consisting of randomly generated pulse sequences (patterns) are interspersed into the population representing the next generation. The process continues iteratively until a specified number of generations or a threshold value for the cost function (fitness) of the best (optimal) solution is reached. After the optimization is complete, a family of final organisms according to various combinations of A, B, and C according to equation 1 are provided to the user or patient, and the pattern(s) that best correspond to user or patient-specific desired outcomes (low pain, low power consumption, low paresthesia) are selected and delivered to the patient. The optimization algorithm can also be toggled on and off (e.g. updates by the physician during check-ups) or set to be on-going with an indefinite endpoint for continuous patient choice.

FIG. 1 is a flow chart of a method 100 of model-based design of optimal temporal patterns of pulse stimulation, for example for use in SCS, in accordance with embodiments of the present disclosure. A stimulation pattern may be represented as a "gene" including a series of pulses representing whether stimulation is on or off over the time interval represented by each pulse. Referring to FIG. 1, the method 100 includes, in step 102, generating a set of random temporal patterns using sequences of pulses (0 and 1).

In step 104, the method 100 includes applying pulse functions to a subject by delivering simulation to the subject or simulating stimulation to the subject using a pattern set. In the first iteration of the method 100, the random temporal pattern generated in step 102 may be used. Multiple patterns may be combined, particularly in the context of the iterative pattern evolution described with reference to steps 104-114 described in the following.

Figure 6A:
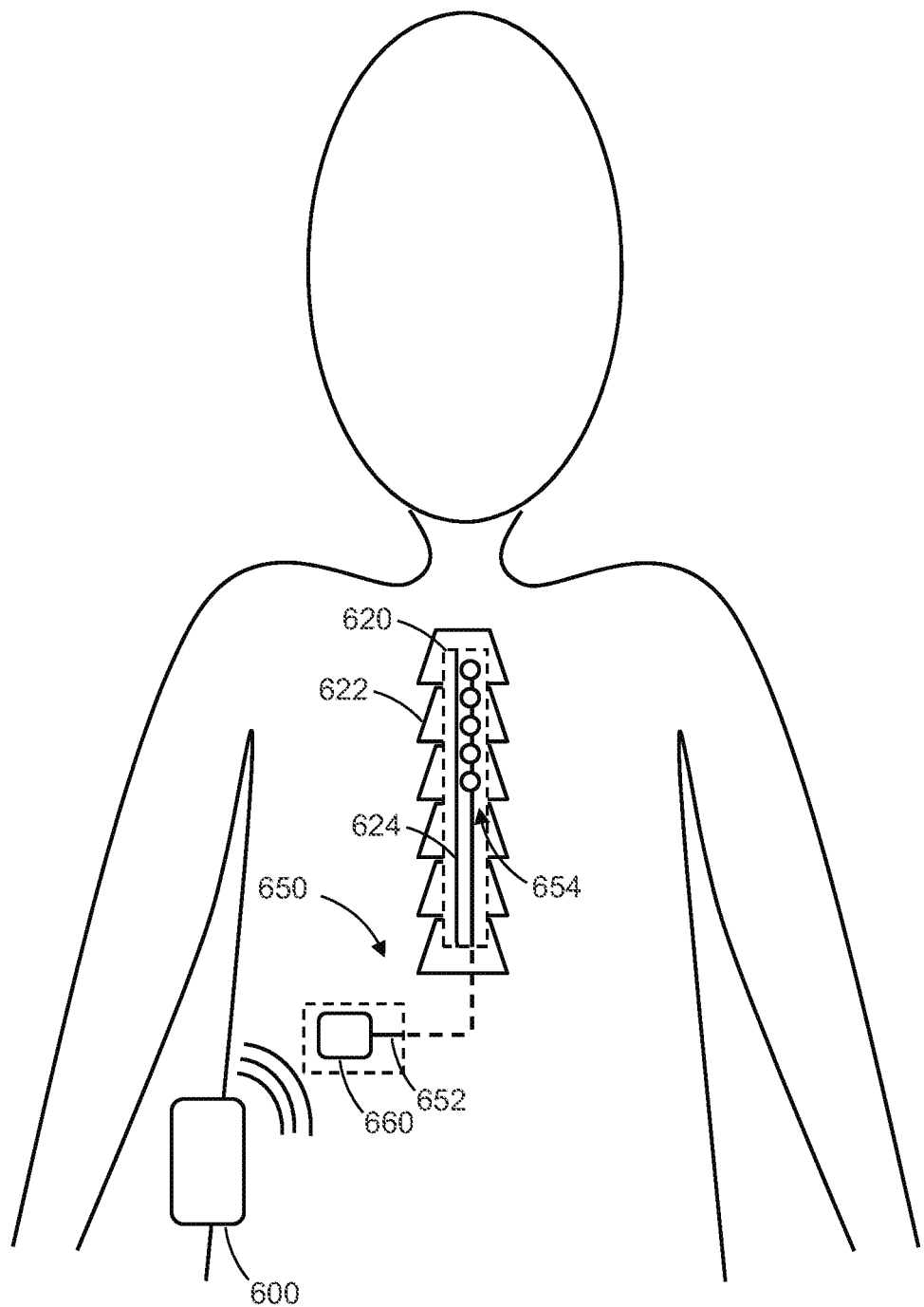
FIG. 6A is an illustration of a remote control device in use to program a spinal cord stimulation (SCS) device according to at least one embodiment.

With regard to delivering stimulation to a subject using a pattern set, the method 100 may be implemented for example by use of an exemplary remote control device 600 to program a spinal cord stimulation (SCS) device 650 to deliver electrical pulse stimulation to a human subject under treatment as shown in FIG. 6A. The remote control device 600 and SCS device 650 are further described below with reference to FIGS. 6A-6B and FIG. 8. Other controller and computing devices for implementation of the method 100 are within the scope of these descriptions. With regard to simulating stimulation to a subject using a pattern set, a computational model can serve as a subject, as described below with reference to FIG. 2, to which simulated stimulation is applied. As such, applying pulse functions can include either or both of delivering electrical pulses to a physical subject and simulating the delivery of pulses to a computational model.

Whether actual stimulation or modeled stimulation is applied, in the method 100 of FIG. 1, step 106 includes using efficacy, efficiency and side effect parameters, according to proxies as measured or simulated, to determine the fitness of the pattern delivered or simulated in step 104.

Step 108 includes ranking and selecting best patterns for preservation, for example by saving for selection for later use as represented in step 116 or for continued optimization in a next generation of patterns for further iteration as represented by the branching of the method 100 to step 112. The selected patterns, referred to as "survivors," are considered those most fit for use (step 116) or for parenting (step 112) next generation patterns, referred to as "offspring."

Step 110 includes determining whether an optimization endpoint or criterion has been reached by the current pattern or patterns under determination in steps 106 and 108. Presuming an optimization endpoint or criterion has not been reached, as represented by "No," the method 100 branches to step 112, which includes constructing a next generation of stimulation patterns by crossing survivor patterns to generate offspring patterns.

The method 100 continues from step 112 into further construction of next generation patterns in step 114 by adding random pulse sequence patterns, referred to as immigrants, and by optionally adding point mutations to the offspring pattern(s) generated in step 112. Thus, step 114 introduces variability into pattern generation for the purpose of facilitating convergence to an optimal solution.

Presuming an optimization endpoint or criterion has been reached, as represented by "Yes" with reference to Step 110, the method 100 branches to step 116, in which optimal patterns are saved for later selection for possible use upon a subject.

The method 100 may continue iteratively in the loop of steps 104-114 until a specified number of generations or until an optimization endpoint or criterion has not been reached. For example, a threshold value for a cost function may be reached. After the optimization is complete, the stimulation patterns deemed to be most optimal by the algorithm are available for delivery to a subject. The optimization algorithm represented by the method 100 may be toggled on and off (e.g., updates by the physician during check-ups) or set to be on-going with an indefinite endpoint.

Figure 2:
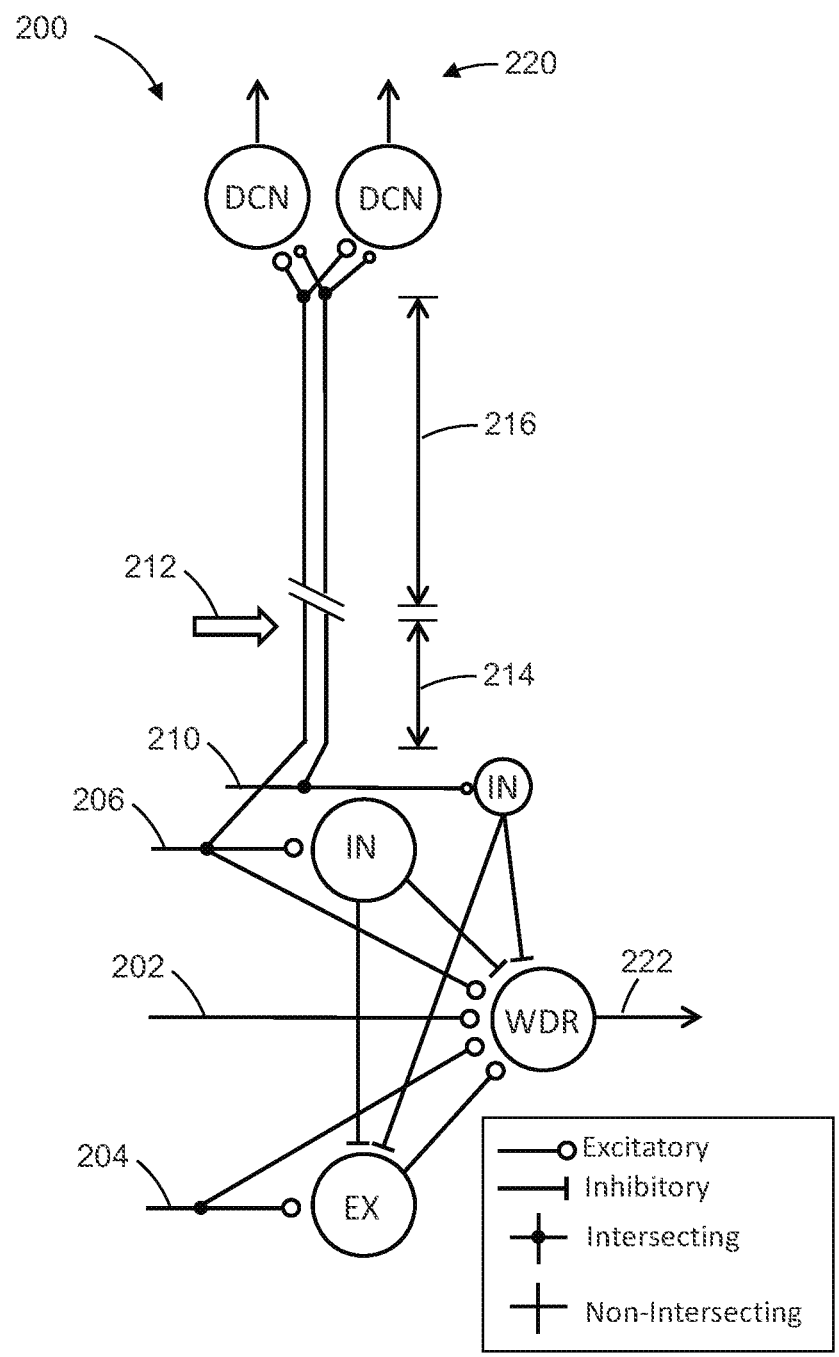
FIG. 2 is a representation of a computational model for use in optimization of temporal stimulation patterns according to at least one embodiment.

FIG. 2 is a representation of a computational model 200 for use in optimization of temporal stimulation patterns according to at least one embodiment. The model 200 includes a network of simulated biophysical neurons that are connected in a manner consistent with existing schemes of the dorsal horn pain processing network as represented in FIG. 2. Inputs to the model will include thirty Aβ fibers, fifteen Aβ fibers 202 and thirty C primary afferent fibers 204 that convey information from the periphery. The thirty Aβ fibers are divided into two sub-populations of fifteen fibers each, with one population of Aβ fibers 206 originating from the "local" source of pain and the other Aβ fibers 210 originating from a "surrounding" receptive field. SCS 212 will be delivered to the network via collaterals of the Aβ fibers to simulate dorsal column fiber activation.

Multiple A/C fibers and excitatory interneurons are used to account for the effect of temporal summation on neuronal activity as well as to add variability to the inputs. To simulate realistic signal propagation from a peripheral or dorsal column nerve fiber, propagation delays based on the conduction velocities of A and C fibers are incorporated into all inputs for all simulations. The assumed distance between the SCS electrode and the dorsal column network will be based on clinical placements of SCS electrodes relative to the target dermatome corresponding to the source of pain. In FIG. 2: IN=Inhibitory Interneuron; EX=Excitatory Interneuron; WDR=Wide-dynamic-range projection neuron; and DCN=dorsal column nucleus neuron. Circular synapses denote excitatory connections. Flat synapses denote inhibitory connections. SCS using the optimization algorithm is delivered via the local and surrounding Aβ-fiber inputs. SCS propagation distance 214 and DCN propagation distance 216 are set according to known clinical and/or patient-specific values. The model 200 includes representations of neurons in the dorsal column nuclei whose activity is believed to correlate with SCS-induced paresthesia. Each dorsal column nucleus neuron receives multiple inputs from the same Aβ/dorsal column fibers affected by SCS. Propagation delays based on clinical distances between the site of assumed SCS and the dorsal column nuclei are applied to SCS inputs for all simulations. Paresthesia related outputs 220 and efficacy related outputs 222 are represented in FIG. 2.

Figure 3A:
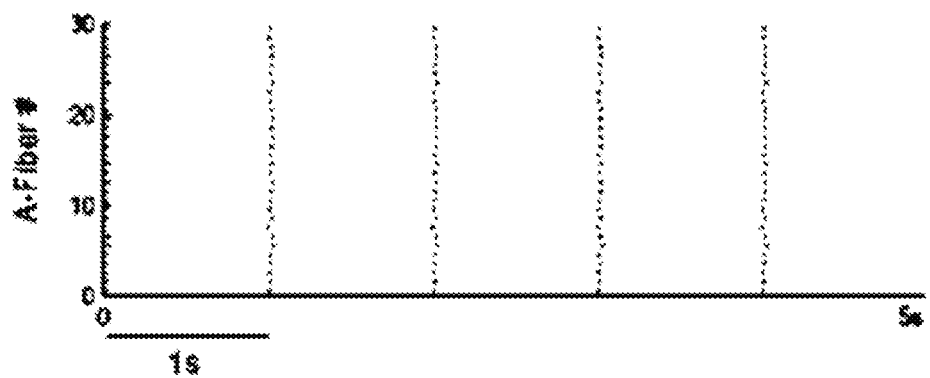
FIG. 3A is a pattern of uniform 1 Hz inputs for A fibers in the model of FIG. 2.
Figure 3B:
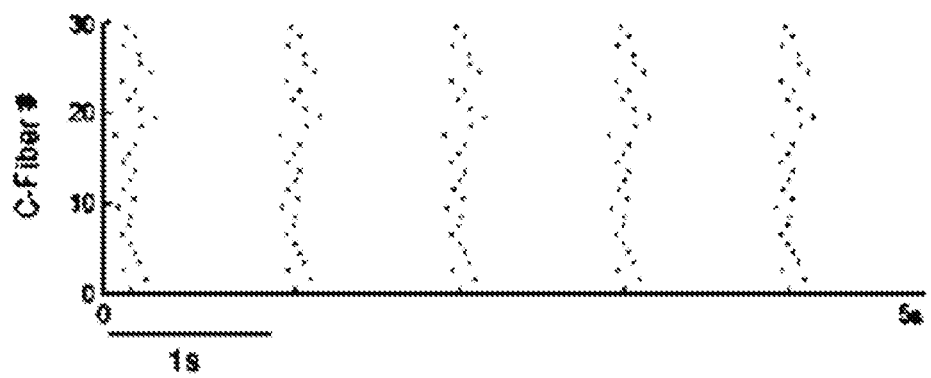
FIG. 3B corresponds to FIG. 3A, for C fibers.
Figure 3C:
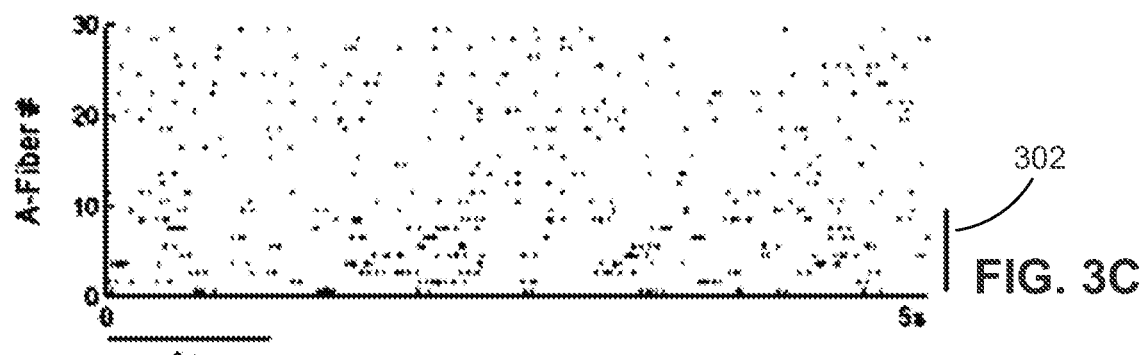
FIG. 3C is field of randomized inputs representing a neuroma (A fibers).
Figure 3D:
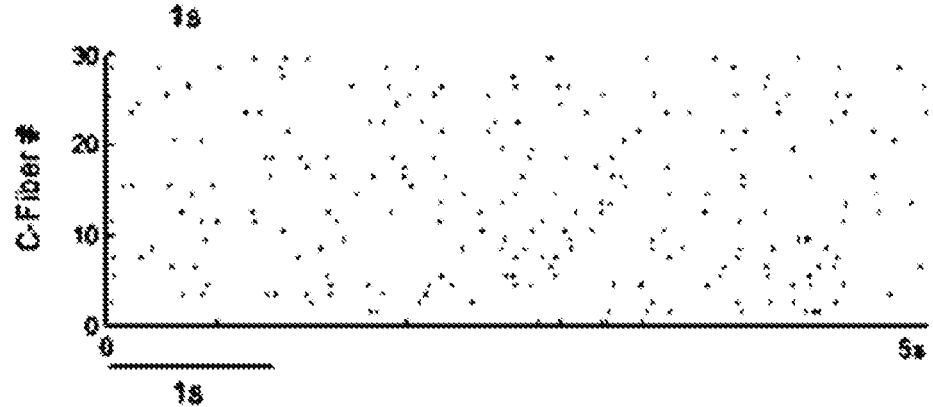
FIG. 3D corresponds to FIG. 3C (C fibers).

FIGS. 3A-3D represent on-going patterns of activity in peripheral primary afferent fibers. Representative uniform 1 Hz inputs (FIG. 3A and randomized inputs representing a neuroma (FIG. 3C) are shown. A five second interval (x-axis) of each is shown for all fiber inputs (y-axis; split by A and C fibers). Each black dot on the graph represents a time point at which a spike is registered by a corresponding input to the model. In FIG. 3C, 30% of the A-fiber inputs exhibit bursting behavior and are denoted by the line segment 302.

Figure 4:
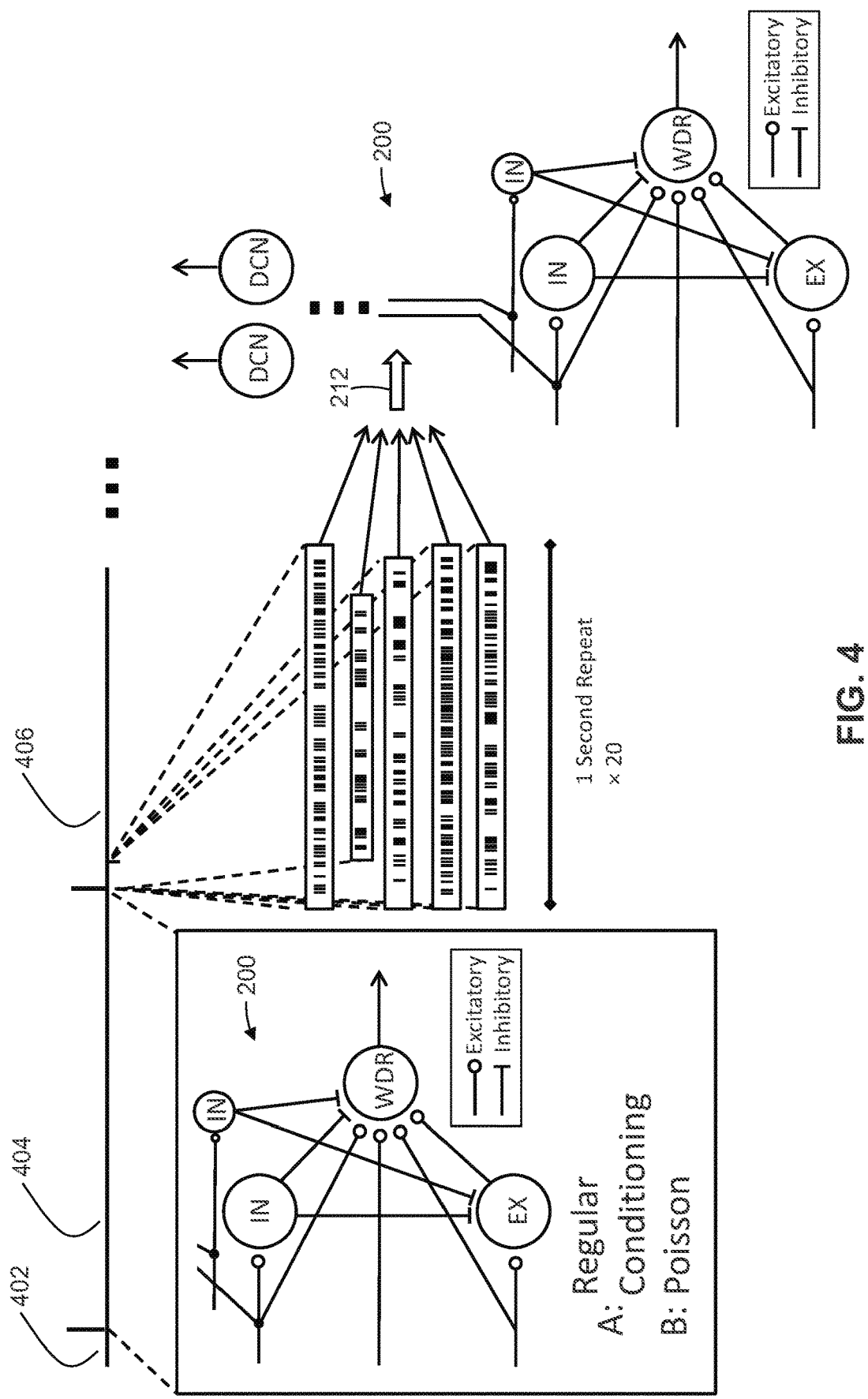
FIG. 4 is a diagrammatic representation of computational optimization according to at least one embodiment.

Computational optimization is conducted as shown in FIG. 4 according to at least one embodiment. Briefly, one second of simulation time 402 is allowed to elapse to allow the model to initialize, and peripheral sensory input consisting of either a constant 1 Hz pulse train synchronized across all fibers or a random spike train based on a Poisson process whose characteristics matching those taken from the firing behavior of a peripheral neuroma (see FIGS. 3A-3D) is delivered for a twenty-second interval 404. SCS 212 using one-second repeats of each temporal stimulation pattern (organism) to be tested within a given generation is delivered for the next twenty-second interval 406 while the output of both the WDR neuron and dorsal column nuclei neurons are recorded. A set of fixed frequency controls where the output of the WDR and dorsal column nuclei neurons in response to and a cost function of constant frequency SCS from 1 Hz to 200 Hz are run for comparison, as current SCS protocols use fixed frequency stimulation. Portions of the model 200 of FIG. 2 are shown in FIG. 4. The algorithm proceeds for example according to the method 100 of FIG. 1.

Figure 5A:
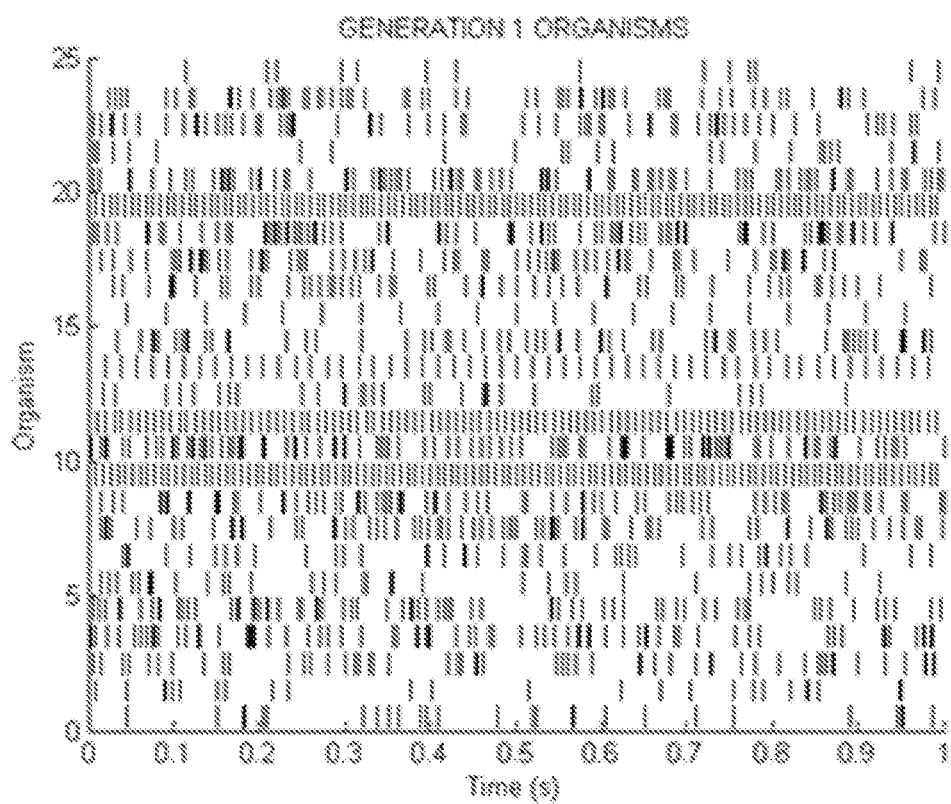
FIG. 5A is a sample of initial populations consisting of twenty five randomly generated pulse streams organisms.

A search heuristic (genetic algorithm) according to at least one embodiment initializes with twenty five randomly generated stimulation patterns, or "organisms," each containing one thousand "pulses" representing one millisecond bins during which an SCS pulse is delivered over a given one second interval; the overall SCS pulse train during a twenty-second stimulation period is built from twenty successive repeats of a given pattern (see FIGS. 4 and 5A). The cost function J corresponding to each stimulation pattern is determined following each simulation run using a weighted sum of the difference between the average firing rate of the WDR neuron during patterned SCS and the firing rate of the WDR neuron during equivalent constant frequency SCS (F), the average frequency of SCS using the organism (S), and the average firing rate of the dorsal column nuclei neurons (P). An exemplary cost function is shown as Equation 1 below:

$$J = A \times F + B \times S + C \times P \quad \text{Equation 1}$$

The weighting terms A, B, and C corresponding respectively to F, S, and P are assigned according to application or patient-specific outcomes, specifically: a patient-specific balance of better efficacy (increase A); better efficiency (increase B); and/or significant paresthesia reduction (increase C). An ideal stimulation train correspondingly has a minimal WDR response, a low equivalent frequency, and/or a minimal dorsal column nuclei neuron response; so patterns of stimulation yielding lower costs (i.e. minimize J) are deemed to be more fit. Following the initial fitness evaluation, organisms are ranked according to their corresponding cost function values, and each subsequent generation is constructed, in at least one embodiment, from: a pre-determined number of the fittest organisms from the current generation ("survivors"); a predetermined number of randomly generated "immigrants;" and "offspring" created from gene crossings from any two organisms (patterns) in the previous generation (see FIG. 5B). To improve diversity among organisms, offspring patterns may be subject to "point mutations," or changes to one or more pulses in a pattern that occur at a fixed frequency across the population (see FIG. 5B). Although all patterns in the previous generation could be represented in the offspring population, patterns that are more fit will have a higher probability of being represented in these crossings than patterns that are less fit. Iterations of the genetic algorithm may be run and populations re-evaluated until a user-defined endpoint or convergence point is reached (see FIG. 5C).

In the crossing of two stimulation patterns, each of two existing patterns is a parent and they are crossed, each contributing some of its elements, to create a subsequent offspring pattern. Crossings between distinct parent organisms are conducted using a uniform cross, in which the probability of any pulse in the offspring originating from either parent is independent of that of any other pulse, i.e., multiple crossover points are used to recombine the two parent patterns. Although all patterns in the previous generation could be represented in these offspring, the probability of a pattern being represented in these crossings is determined using a random decaying exponential distribution built such that patterns that are more fit (i.e., produce lower value of the cost function) have a higher probability of being selected for uniform crosses than less fit patterns.

Figure 5B:
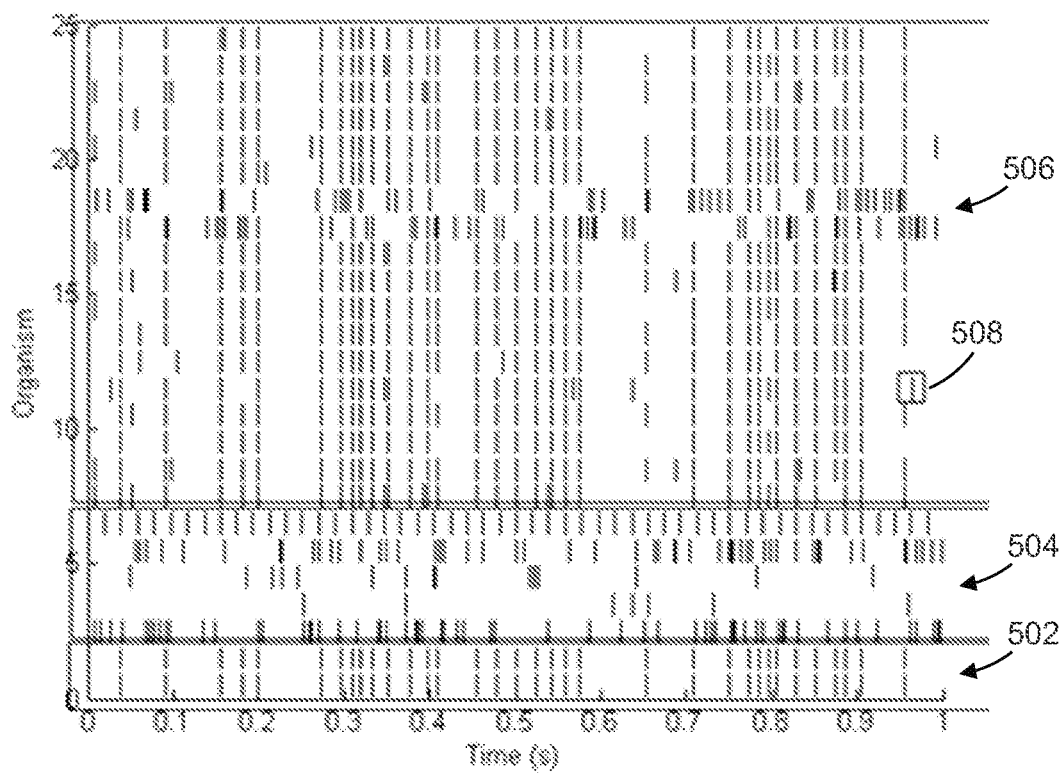
FIG. 5B is a set of twenty five organism patterns in a subsequent generation including survivors, immigrants and offspring patterns.
Figure 5C:
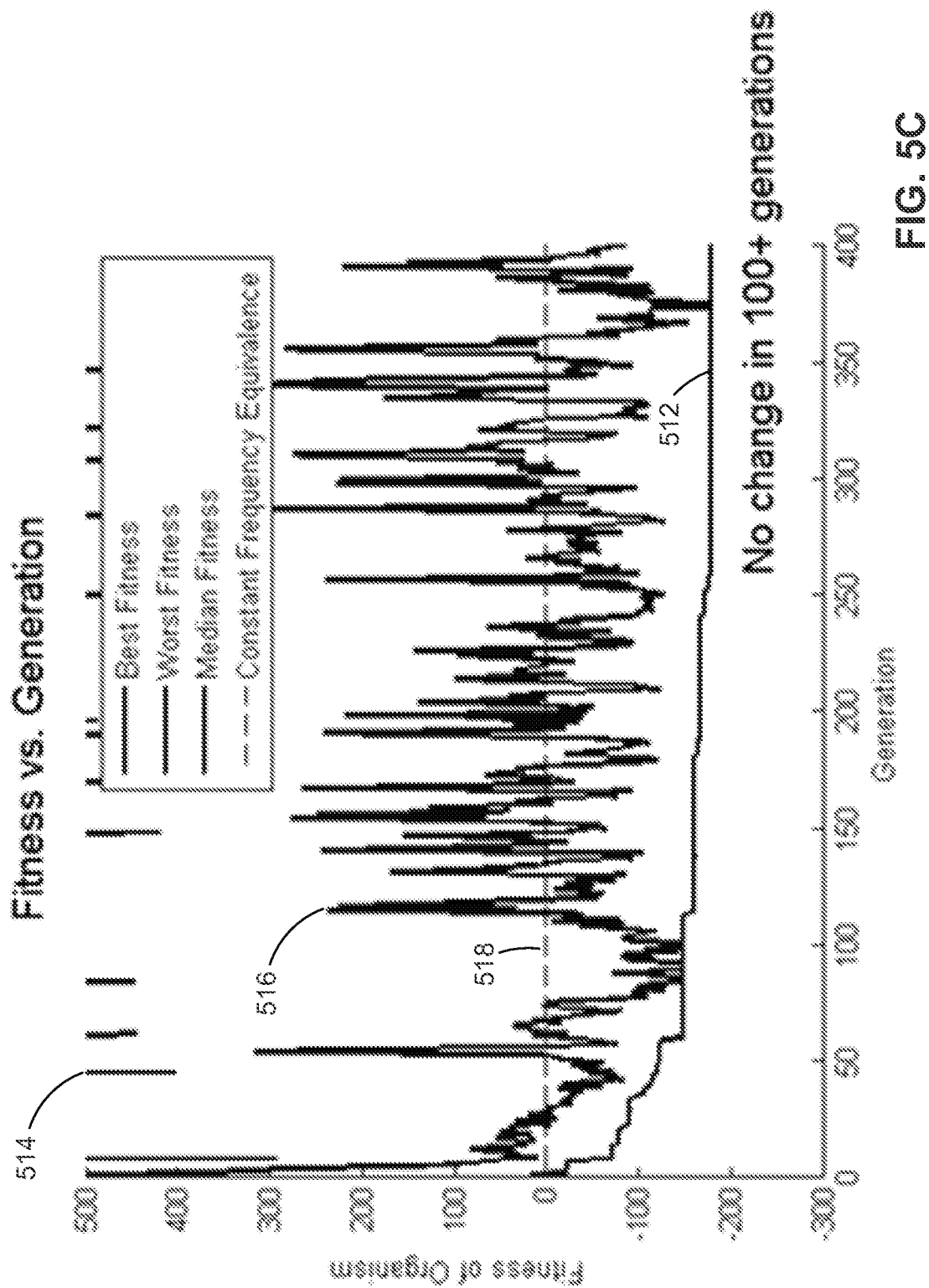
FIG. 5C is a plot of fitness scores across four hundred successive generations.

FIGS. 5A-5C show sample population of patterns and optimization progression. FIG. 5A is a sample of initial populations consisting of twenty five randomly generated pulse streams ("organisms"), where each dash, corresponding to a binary "1," represents a one millisecond time interval during which active stimulation occurs within a one second long repeating pattern.

FIG. 5B is a set of twenty five organism patterns in a subsequent generation consisting of: a pre-determined number of survivors 502, defined as the most fit organisms from the prior generation; a pre-determined number of randomly generated immigrant patterns 504; and offspring patterns 506 of the organisms in the previous generation that may or may not be subject to point mutations 508.

FIG. 5C is a plot of fitness scores across four hundred successive generations. Plots for best fitness organisms 512, worst fitness organisms 514, and medium fitness organisms 516 are shown along with a constant frequency equivalence plot 518. The depicted optimization proceeds for a specified number of generations and/or until the fitness of the most optimal organism no longer improves.

SCS optimization and delivery may be carried out as an algorithm on a separate platform, such as a CPU, desktop or laptop computer, a tablet, a smartphone, or a comparable device, or it can be carried out as software within a spinal cord stimulation pulse generator device.

These descriptions relate also to the use of a remote controller to program a spinal cord stimulation (SCS) device with non-regular temporal patterns of stimulation generated using a mathematic search heuristic such as the genetic algorithm described above with reference to FIG. 1. Simulation experiments using a biophysical model of the pain processing circuit in the dorsal horn have indicated that SCS using non-regular temporal patterns including features such as gaps, bursts, and irregular inter-pulse intervals (FIGS. 7A and 7C) generated using the genetic algorithm can be more effective or efficient at suppressing the activity of WDR neurons responsible for the transmission of pain to the brain than SCS at the equivalent frequency using a constant IPI.

An SCS system and method according to at least one embodiment each is provided as or by a remote control device to program an SCS device. FIG. 6A is an illustration of a remote control device 600 in use to program the SCS device 650 according to at least one embodiment.

Figure 6B:
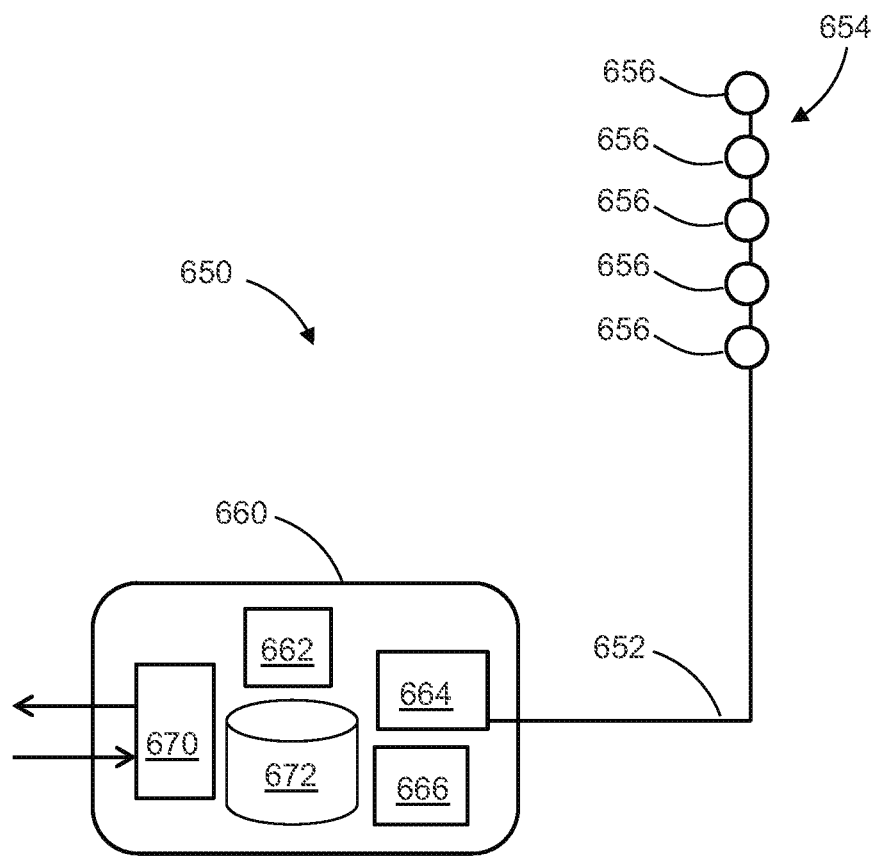
FIG. 6B is a block diagram of the SCS device of FIG. 6A.
Figure 7:
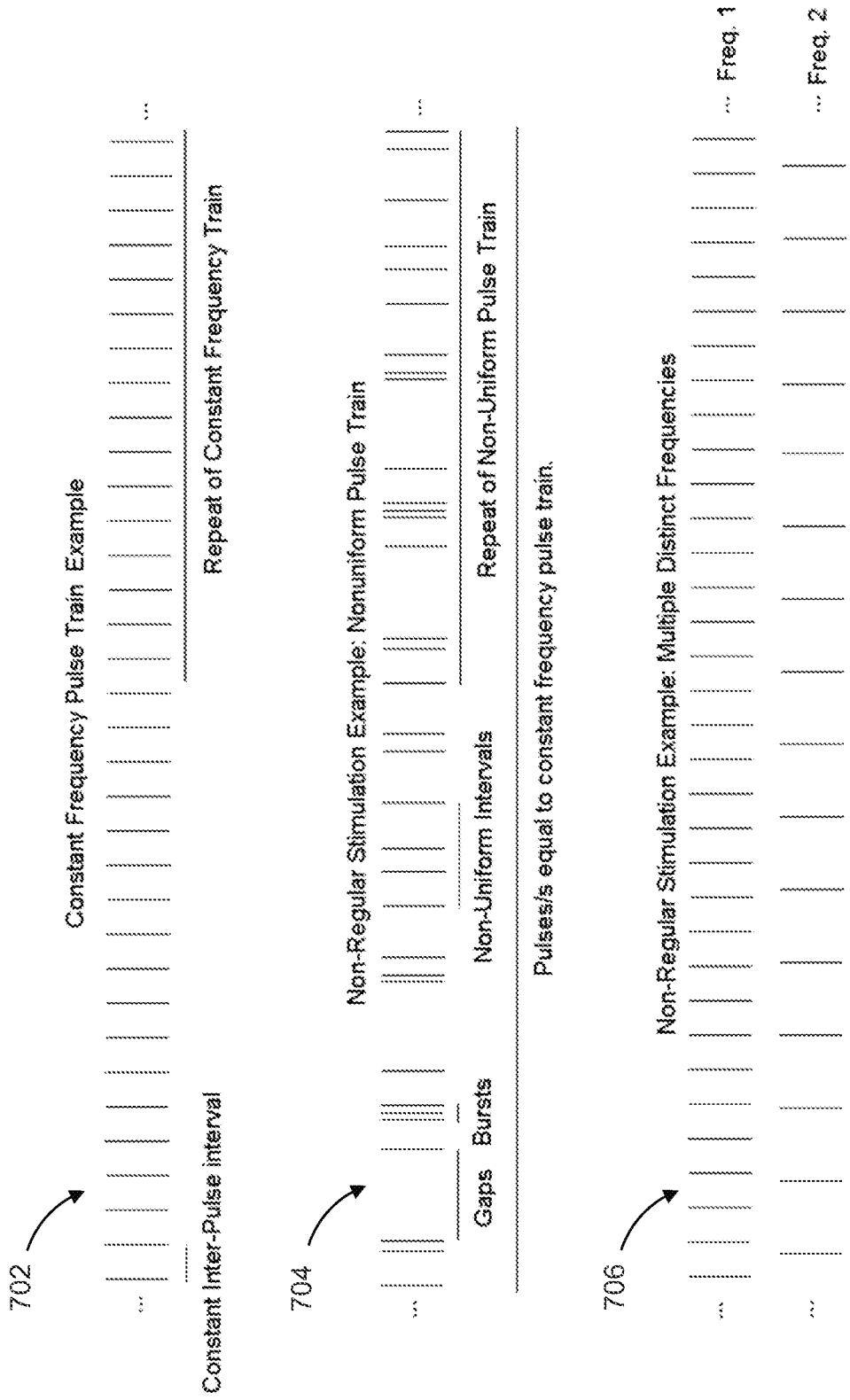
FIG. 7 is a set of examples of non-regular stimulation patterns including non-uniform temporal patterns and multiple frequency SCS patterns compared to a regular, constant frequency pattern.
Figure 8:
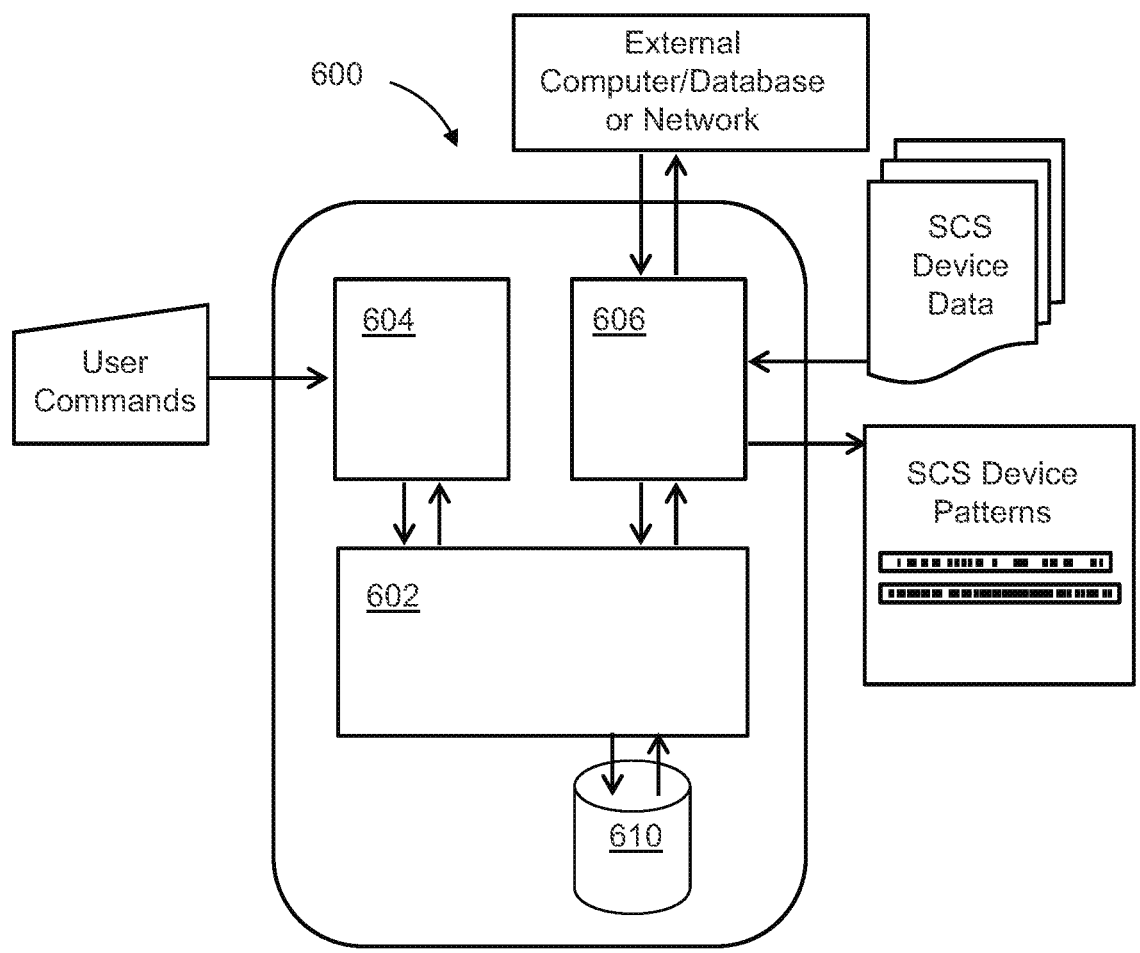
FIG. 8 is a block diagram of the remote control device of FIG. 6A.

FIG. 8 is a block diagram of the remote control device 600. The remote control device 600 is shown in FIG. 8 as a stand-alone remote electronic device including of an internal processor 602, a user interface 604, and wired or wireless input/output ports 606 that are capable of communicating with the SCS device 650 (FIGS. 6A-6B). The internal processor 602 (FIG. 8) is capable of downloading, uploading, storing in a storage device 610, and running computer codes and other data content necessary for the generation of stimulation patterns using search heuristics, and the transmission of such patterns to the SCS device 650. For example, the internal processor 602 sends and receives temporal pattern information and data to and from an external computer/database. The stimulation patterns may be used by the SCS device to deliver non-regular stimulation, where non-regular stimulation includes non-uniform temporal patterns and/or combinations of multiple, distinct frequencies of constant stimulation delivered simultaneously (see for example FIG. 7). The internal processor 602 can either be custom-designed for this purpose and as part of a stand-alone device as illustrated in FIG. 6A. Other embodiments can be realized as a program on a computer, laptop computer, smartphone, personal desktop assistant (PDA), tablet, or other electronic device capable of remotely communicating with and controlling an SCS device pre- or post-implantation.

Figure 9:
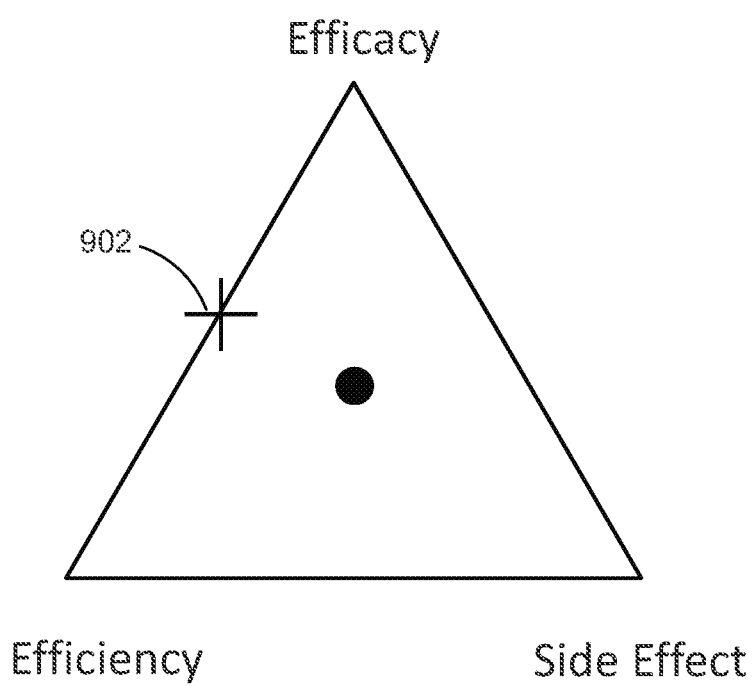
FIG. 9 is a user-interface graphic in which the user moves a cursor to determine the relative weights of efficacy, efficiency, and side effects in SCS pattern optimization.

The user interface 604 (FIG. 8) receives user input and displays data to the user, such as the current patterns and combinations being delivered and/or measured biological indicators of pain such as but not limited to the firing rate of WDR neurons, and permit the user to program the search heuristic or the temporal pattern to be output by the device through a built-in hardware interface such as a touch screen, buttons/keyboard, voice command, or other such methods. In addition, the user interface 604 will allow the user to toggle the search heuristic algorithm on and off on the device and/or to alter the weights of parameters (e.g. efficacy of stimulation, power consumption efficiency, side effects) by which the search heuristic determines the temporal patterns or combinations of frequencies to be delivered. For example, as shown in FIG. 9, the user interface 604 (FIG. 8) may be used to adjust the coefficients A, B and C in Equation 1 above by which the sensitivity of the cost function J to each parameter F, S and P is varied.

Advantageously, the user interface 604 allows the user to configure which active electrode contact(s) will deliver which temporal pattern(s) and/or frequencies. Communication with the SCS device 650 or an external system may occur through a direct wired link or wirelessly through the use of radiofrequency (RF) transmission, Bluetooth, a wireless local area network (WLAN), or similar protocol. The remote control device 600 may send information or programming instructions to the SCS device 650 and receive information from the SCS device 650 regarding the current stimulation parameters such as the pattern(s) being delivered through one or more specific electrode contacts and information regarding the state of the patient, such as a neural signal corresponding to the patient's pain level.

FIG. 6A also illustrates an anatomic view of the SCS device 650 implanted to stimulate targeted neurological tissue of a human subject in accordance with at least one embodiment. The subject may be suffering from a neurological disorder, such as chronic pain or other condition. FIG. 6B is a block diagram of the SCS device of FIG. 6A. The SCS device 650 includes an electrical cord 652 and an array 654 of multiple electrodes 656. Five electrodes 656 are expressly shown but any number of electrodes can be included. The electrode array 654 is shown operatively positioned in FIG. 6A in the epidural space 620 of a vertebral column 622 of the subject. The electrode array 654 is positioned at the site of nerves that are the targets of stimulation, e.g., along the spinal cord 624. Alternatively, the electrode array 654 may be suitably positioned in any other location for desired electrical stimulation of targeted neurological tissue. The cord 652 may include multiple lines or leads such that different or the same electrical signals can be provided to the electrodes 656.

The SCS device 650 includes a control module 660 from which the cord 652 extends to any desired treatment location. As shown in FIG. 6A, the control module 660 of the SCS device 650 may be carried by the subject, for example in a pocket or specially adapted pouch, or may be suitably implanted within the subject such as, but not limited to, implantation within the abdomen or other body portion. The electrical cord 652 is operatively connected to an output of the control module 660 to deliver stimuli patterns to the desired subject via the electrode array 654.

As shown in FIG. 6B, the control module 660 of the SCS device 650 includes a local controller 662, a pulse generator 664, a power source 666, an input/output device 670, and a memory storage device 672. The local controller 662 may include a processor that runs software, firmware, or combinations thereof, for example stored on the memory storage device 672, for implementing functionality described herein. The controller 662 is operatively connected to the pulse generator 664 for controlling the pulse generator to generate electrical signals for applying patterns of electrical stimulation to targeted neurological tissue. The output signals of the pulse generator are conveyed by the electrical cord 652 to the electrode array 654 for electrical stimulation at targeted neurological tissue. The power source 666, such as a battery, supplies power to the local controller 662 and the pulse generator 664 and any other local devices as needed. The control module 660 may communicate with the remote control device 600 via the input/output device 670 by any suitable communication link (e.g., a wired, wireless, or optical communication link). The communication link may also facility battery recharging.

A clinician may interact with a user interface of the remote control device 600 for programming the output of the implanted pulse generator 664, including the electrodes that are active, the stimulation pulse amplitude, the stimulation pulse duration, the stimulation pattern (including pulse repetition frequency), and the like applied via each electrode 656. A patient may also interact with the user interface 604 of the remote control device 600 (FIG. 8) to, for example, provide information feedback regarding the patient experience, including, for example, whether side effects are experienced and whether pain symptoms are improved or worsened. The patient may interact with the user interface for selecting among a set of pre-programmed stimulation parameter sets. These sets may have been programmed or otherwise set by the clinician and stored in the storage device 610 of the remote control device 600 or the memory storage device 672 of the control module 660 of the SCS device 650.

In at least one embodiment, the remote control device 600 determines or receives temporal SCS patterns and communicates information for administering the temporal patterns to the SCS device 650, which applies the prescribed temporal pattern(s) of electrical stimulation to targeted neurological tissue of the subject.

In at least one embodiment, a doctor, clinician, or other qualified user will use the remote control device 600 to program the SCS device 650 to deliver non-regular stimulation to a patient (FIG. 6A). Non-regular stimulation entails non-uniform temporal patterns of combinations of multiple, distinct frequencies that are either initially programmed into the device or derived using an search heuristic such as genetic algorithm or a map of stimulation effects (efficacy, efficiency, side effects) by combination (FIG. 7). Following device implantation and activation, the user may then elect to use pre-loaded stimulation paradigms as described or to toggle a built-in search heuristic to optimize temporal patterns or frequency combinations. This optimization may be based on a cost function such as Equation 1 described above. The total "cost" of therapy (J) as a function of measures of efficacy (F), efficiency (S), or side effects (P) weighted by preference towards improved efficacy (A), stimulation efficiency (B), or side effects (C). In at least one embodiment, an internal database maps possible combinations of multiple frequencies to efficacy, efficiency, or side effect values that will result from stimulation using those combinations, or another operation.

With reference to Equation 1, a user may adjust the absolute values of A, B, and C or their relative weightings (i.e. the ratio between A and B) on a sliding scale, numeric pad, or other display featured on the user interface as shown in FIG. 9. Setting of the ratios of A, B, and C may cause the control device 600 to program the SCS device 650 with pre-determined non-regular stimulation paradigms optimized for the specific values/ratio of A, B, and C or a group of temporal patterns and frequency combinations between which the patient may be allowed to switch. In a closed-loop device, setting the ratio may act to configure an on-board search heuristic (optimization algorithm, database) in the SCS device to generate and optimize non-regular patterns or combinations of frequencies according to the desired cost function.

The user may also determine using the user interface which electrode contact(s) will deliver which temporal pattern(s) and frequencies. Once the user indicates that programming (pre-determined temporal pattern or optimization) is complete, the control device 600 sends a signal through its communication interface to the SCS device 650 that toggles stimulation using the non-regular patterns of stimulation and possibly optimization. At any time afterwards, a qualified user may override the system through the user interface and toggle the optimization algorithm on and off, alter the parameters of the optimization cost function within reasonable limits, and/or change the temporal pattern(s) being delivered by the SCS device 650 using the remote control device 600 and associated graphical interface. In addition, if the system detects a biological signal indicating an unsafe condition caused by stimulation, then the system may conduct a safety override by defaulting to a pre-configured set of "safe" patterns, toggling the optimization algorithm on/off, or altering the search heuristic (e.g. skipping certain patterns or combinations, reverting to a previous pattern or combination).

FIG. 7 is a set of examples of non-regular stimulation patterns including non-uniform temporal patterns 704 and multiple frequency SCS patterns 706 compared to a regular, constant frequency pattern 702. In the non-uniform temporal patterns 704, although the numbers of pulses per unit of time may be the same as shown in constant frequency pattern 702, the non-uniform temporal patterns may possess additional features such as gaps, bursts, and/or irregular inter-pulse intervals and may be generated or altered through the use of an optimization search heuristic. In the multiple frequency SCS patterns 706, two (or more) distinct frequencies may be delivered simultaneously to the patient through the same electrode, and the frequencies chosen represent a pre-determined combination whose effects meet the efficacy, efficiency, and side effect parameters specified by the user. The frequencies chosen for the patterns 706 may or may not be multiples/factors of each other, and the constant frequency pulse train in the patterns 702 may or may not represent the average frequency of the combinations shown in the patterns 706.

In one example of user direct entry of cost function parameter weighting coefficients (A, B, C) the user enters the raw values for the weightings of efficacy, efficiency, and side effects that correspond to patterns or frequency combinations optimized for that set of values. The points allocated may be constrained by a hard limit (for example, the total points may be limited by a sum total, such as a numeric value of 9 or another amount) or recalculated into ratios by the device.

FIG. 9 is a user-interface graphic in which the user moves a cursor 902 on a sliding scale to determine the relative weights of efficacy, efficiency, and side effects that correspond to stimulation optimized for that set of values. The design of the sliding scale may be fixed (as shown or otherwise) or configurable by the user. Following value/ratio selection, the remote control device 600 will output stimulation (non-uniform patterns or combinations of frequencies) optimized to the desired settings according to the search heuristic (cost function, internal database). These examples of user input are not fully inclusive of all possible GUI features or GUI designs.

Figure 10:
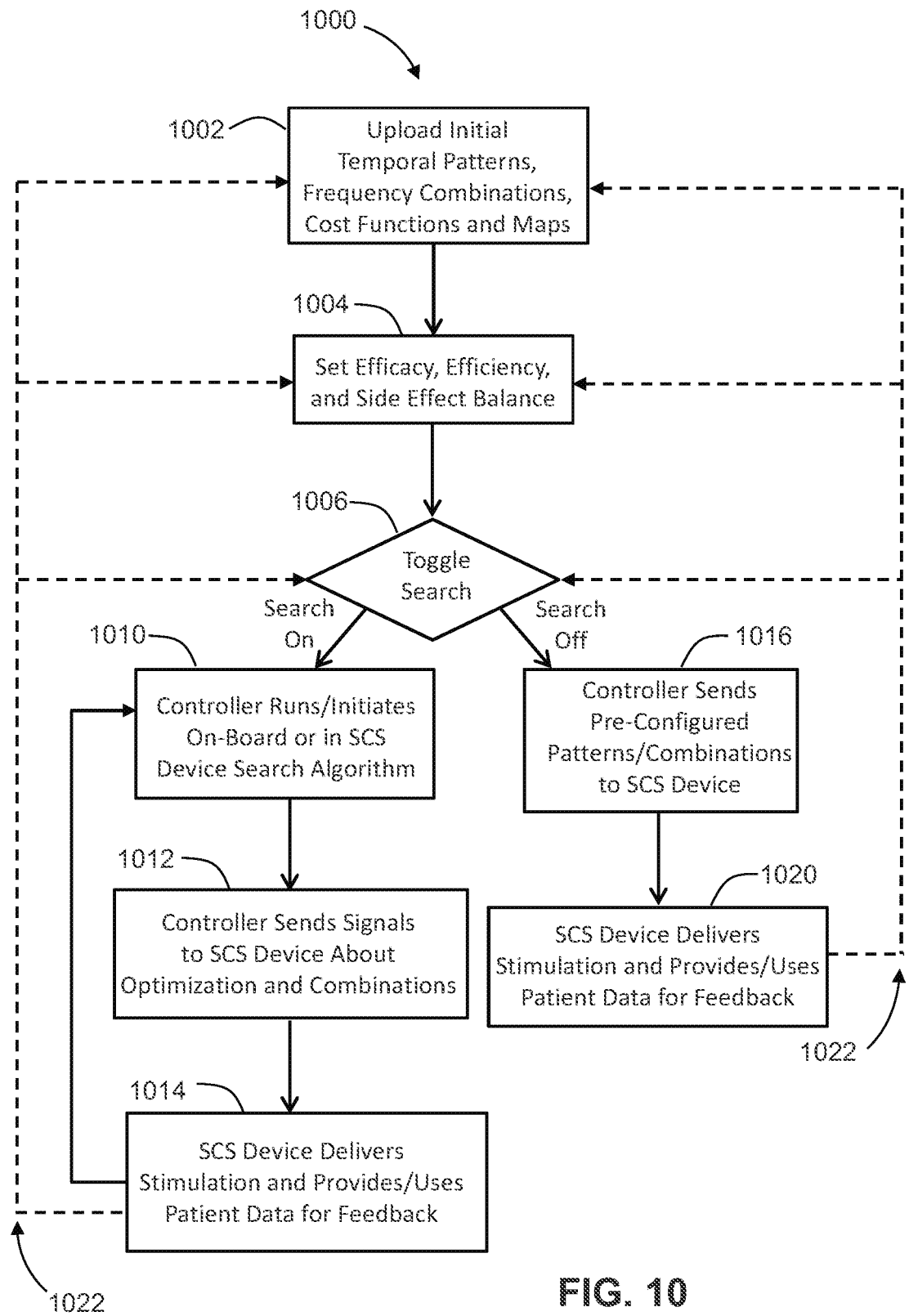
FIG. 10 is a flow chart detailing a method by which, according to at least one embodiment, the remote control device and the SCS device of FIG. 6A deliver and optimize SCS patterns.

FIG. 10 is a flow chart detailing a method 1000 by which, according to at least one embodiment, a controller such as the remote control device 600 delivers pre-configured non-regular temporal patterns/frequency combinations to a stimulation device such as the SCS device 650 and/or to configure an optimization search heuristic used to generate non-regular temporal patterns and/or find appropriate frequency combinations. Pre-configured non-regular patterns and/or frequency combinations can be delivered or searching for optimized patterns and combinations using an on-board search algorithm can be conducted.

In the method 1000, step 1002 includes uploading initial temporal patterns, frequency combinations, cost functions and maps. Step 1004 includes setting efficacy, efficiency, and side effect balance. Step 1006 includes toggling a search, for example by initiating the genetic algorithm described above with reference at least to FIGS. 1 and 5A-5C.

The method 1000 continues, if searching is toggled on in step 1006, in step 1010 which includes running or initiating the search algorithm at the controller or stimulation device. In step 1012, the controller sends signals to stimulation device about optimization and combinations. In step 1014, the stimulation device delivers stimulation and provides and/or uses patient data for feedback. As the search continues, the method 1000 loops back to step 1010 from step 1014 iteratively.

If searching is toggled off in step 1006, the method 1000 continues, in step 1016 in which the controller sends pre-configured patterns/combinations to the stimulation device. In step 1020, the stimulation device delivers stimulation and provides and/or uses patient data for feedback, which occurs as long as treatment is prescribed or desired.

User or system prompted override branches 1022 in FIG. 10 represent that the iterative search loop (steps 1010, 1012 and 1014) and the treatment in step 1020 can be interrupted and control can return to any previous stage by user or practitioner actions prompting override.

Particular embodiments and features have been described with reference to the drawings. It is to be understood that these descriptions are not limited to any single embodiment or any particular set of features, and that similar embodiments and features may arise or modifications and additions may be made without departing from the scope of these descriptions and the spirit of the appended claims.

What is claimed is:

1. A method of optimizing temporal pulse patterns for electrical pulse stimulation delivery to a subject, the method comprising:

generating optimized temporal pulse patterns using a computational model of the pain circuit in the spinal cord by simulating delivery of pulse patterns to the computational model; and programming a stimulation device to deliver electrical pulse stimulation to the subject according to the optimized temporal pulse patterns.

2. The method according to claim 1, wherein generating optimized temporal pulse patterns using a computational model by simulating delivery of pulse patterns to the computational model comprises iteratively constructing successive generations of the pulse patterns by determining a fitness of each particular pulse pattern.

3. The method according to claim 2, wherein determining the fitness of each particular pulse pattern comprises determining an efficacy parameter, an efficiency parameter, and a side-effect parameter.

4. The method according to claim 3, wherein determining the fitness of each particular pulse pattern comprises minimizing a cost function (J) defined as $J=A\times F+B\times S+C\times P$; wherein:
A, B, and C are numerical coefficients;
F is the efficacy parameter;
S is the efficiency parameter; and
P is the side effect parameter.

5. The method according to claim 3, wherein the subject is a human patient and the side effect parameter is determined at least in part using feedback from the human patient.

6. The method according to claim 2, wherein iteratively constructing successive generations of the pulse patterns comprises:
causing delivery of electrical pulse stimulation to the subject according to any particular generation of temporal pulse patterns;
measuring efficacy, efficiency and side-effect parameters affected by the delivery of electrical pulse stimulation to the subject according to the particular generation temporal pulse patterns;
determining a fitness of the particular generation temporal pulse patterns using the measured efficacy, efficiency and side-effect parameters thereof; and
generating a next generation temporal pulse patterns using the particular generation temporal pulse patterns according to the determined fitness of the particular generation temporal pulse patterns.

7. The method according to claim 1, wherein:
the optimized temporal pulse patterns are generated by a computer using the computational model; and
programming the stimulation device to deliver the optimized temporal pulse patterns comprises communicating the optimized temporal pulse patterns from the computer to a remote control device.

8. The method according to claim 7, wherein the remote control device transmits the optimized temporal pulse patterns to the stimulation device.

9. The method according to claim 1, wherein the stimulation device comprises multiple electrodes each for placement in proximity to a respective portion of the subject.

10. The method according to claim 9, wherein programming the stimulation device comprises programming respective instructions for delivery of electrical pulse stimulation by each of the multiple electrodes.

11. The method according to claim 1, wherein the computational model includes a network of simulated biophysical neurons connected in a manner consistent with a physical dorsal horn pain processing neuron network.

12. The method according to claim 1, wherein the computational model includes representations of neurons in the dorsal column nuclei (DCN).

13. A system configured to optimize temporal pulse patterns for electrical pulse stimulation delivery to a subject, the system including at least one processor configured for use to implement an algorithm comprising:
generating optimized temporal pulse patterns using a computational model of the pain circuit in the spinal cord by simulating delivery of pulse patterns to the computational model; and
programming a stimulation device to deliver electrical pulse stimulation to the subject according to the optimized temporal pulse patterns.

14. The system according to claim 13, wherein generating optimized temporal pulse patterns using a computational model by simulating delivery of pulse patterns to the computational model comprises iteratively constructing successive generations of the pulse patterns by determining a fitness of each particular pulse pattern.

15. The system according to claim 14, wherein determining the fitness of each particular pulse pattern comprises determining an efficacy parameter, an efficiency parameter, and a side-effect parameter.

16. The system according to claim 15, wherein determining the fitness of each particular pulse pattern comprises minimizing a cost function (J) defined as $J=A\times F+B\times S+C\times P$; wherein:
A, B, and C are numerical coefficients;
F is the efficacy parameter;
S is the efficiency parameter; and
P is the side effect parameter.

17. The system according to claim 15, wherein the subject is a human patient and the side effect parameter is determined at least in part using feedback from the human patient.

18. The system according to claim 14, wherein iteratively constructing successive generations of the pulse patterns comprises:
causing delivery of electrical pulse stimulation to the subject according to any particular generation of temporal pulse patterns;
measuring efficacy, efficiency and side-effect parameters affected by the delivery of electrical pulse stimulation to the subject according to the particular generation temporal pulse patterns;
determining a fitness of the particular generation temporal pulse patterns using the measured efficacy, efficiency and side-effect parameters thereof; and
generating a next generation temporal pulse patterns using the particular generation temporal pulse patterns according to the determined fitness of the particular generation temporal pulse patterns.

19. The system according to claim 13, wherein:
the optimized temporal pulse patterns are generated by the at least one processor using the computational model; and
programming the stimulation device to deliver the optimized temporal pulse patterns comprises communicating the optimized temporal pulse patterns to a remote control device.

20. The system according to claim 19, wherein the remote control device transmits the optimized temporal pulse patterns to the stimulation device.

21. The system according to claim 13, wherein the stimulation device comprises multiple electrodes each for placement in proximity to a respective portion of the subject.

22. The system according to claim 21, wherein programming the stimulation device comprises programming respective instructions for delivery of electrical pulse stimulation by each of the multiple electrodes.

23. The system according to claim 13, wherein the computational model includes a network of simulated biophysical neurons connected in a manner consistent with a physical dorsal horn pain processing neuron network.

24. The system according to claim 13, wherein the computational model includes representations of neurons in the dorsal column nuclei (DCN).

\* \* \* \* \*